United States Patent
Menard et al.

(10) Patent No.: US 6,960,998 B2
(45) Date of Patent: *Nov. 1, 2005

(54) BI-DIRECTIONAL WIRELESS DETECTION SYSTEM

(75) Inventors: Raymond J. Menard, Hastings, MN (US); Curtis E. Quady, Burnsville, MN (US)

(73) Assignee: Royal Thoughts, LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/757,367

(22) Filed: Jan. 14, 2004

(65) Prior Publication Data

US 2004/0201475 A1 Oct. 14, 2004

Related U.S. Application Data

(63) Continuation of application No. 09/956,474, filed on Sep. 19, 2001, now Pat. No. 6,759,956, which is a continuation of application No. 09/384,165, filed on Aug. 27, 1999, now Pat. No. 6,356,192.
(60) Provisional application No. 60/105,493, filed on Oct. 23, 1998, and provisional application No. 60/135,862, filed on May 25, 1999.

(51) Int. Cl.$^7$ .............................................. H04Q 7/00
(52) U.S. Cl. .............................. 340/539.19; 340/539.1; 340/531; 340/517; 340/533; 340/825.36; 340/825.49
(58) Field of Search .................. 340/539.1, 539.14, 340/539.19, 506, 531, 517, 511, 524, 537, 533, 3.1, 825.36, 825.49

(56) References Cited

U.S. PATENT DOCUMENTS 3,843,841 A 10/1974 Rubinstein
3,969,709 A 7/1976 Isaacs et al.
4,067,411 A 1/1978 Conley et al.

(Continued)

FOREIGN PATENT DOCUMENTS

| FR | 2758403 A1 | 7/1998 |
| GB | 2285704 | 7/1995 |
| WO | WO-00/25284 A2 | 5/2000 |

OTHER PUBLICATIONS

*Skyroute Communications,* http://www.sur-gard.com/skyroute.htm,(1974),pp. 1–4.
"21st Century Emergency Safety Communication Policy", *comCARE Alliance,* http://www.comcare.org/21c199.htm, (2000),pp. 1–3.
"AlarmNet–A Original Alarmnet", *AlarmNet,* http;//www.a-demco.com/AlarmNet/AlarmNetA.htm,(2000),pp. 1–2.
"AlarmNet–C Control Channel Cellular", *AlarmNet,* http://www.ademco.com/AlarmNet/AlarmNetC.htm,(2000),2 pages.
"AlarmNet–M Mobitex System", *AlarmNet,* http://www.a-demco.com/AlarmNet/AlarmNetM.htm,(2000),p. 1,
"allNetDevices:—Geoworks, Openware End Patent Fight", *allNetDevices,* http://www.devices.internet.com,(2000),1 page.

(Continued)

*Primary Examiner*—Daryl C Pope
(74) *Attorney, Agent, or Firm*—Schwegman, Lundberg, Woessner & Kluth, P.A.

(57) ABSTRACT

A system is described for detecting at least one event of interest. The system comprises a detector, a programmable controller, and a network. Upon detection of an event of interest, the detector communicates that information to the programmable controller through the network. The programmable controller allows a user, who may be in diverse geographic locations, to control the detector.

36 Claims, 9 Drawing Sheets

U.S. PATENT DOCUMENTS

| | | | |
|---|---|---|---|
| 4,237,344 A | 12/1980 | Moore | |
| 4,284,849 A | 8/1981 | Anderson et al. | |
| 4,303,801 A | 12/1981 | Anderson et al. | |
| 4,463,292 A | 7/1984 | Engelmann | |
| 4,531,527 A | 7/1985 | Reinhold, Jr. et al. | |
| 4,772,876 A * | 9/1988 | Laud | 340/539 |
| 4,789,859 A | 12/1988 | Clarkson et al. | |
| 4,843,377 A | 6/1989 | Fuller et al. | |
| 4,856,047 A | 8/1989 | Saunders | |
| 4,908,600 A | 3/1990 | Martinez | |
| 4,993,059 A | 2/1991 | Smith et al. | |
| 4,994,787 A | 2/1991 | Kratt et al. | |
| 5,016,172 A | 5/1991 | Dessertine | |
| 5,025,374 A | 6/1991 | Roizen et al. | |
| 5,062,147 A | 10/1991 | Pickett et al. | |
| 5,081,667 A | 1/1992 | Drori et al. | |
| 5,128,979 A | 7/1992 | Reich et al. | |
| 5,144,700 A | 9/1992 | Martin | |
| 5,179,571 A * | 1/1993 | Schilling | 375/1 |
| 5,195,126 A | 3/1993 | Carrier et al. | |
| 5,223,844 A | 6/1993 | Mansell et al. | |
| 5,228,449 A | 7/1993 | Christ et al. | |
| 5,276,728 A | 1/1994 | Pagliaroli et al. | |
| 5,278,539 A | 1/1994 | Lauterbach et al. | |
| 5,319,355 A | 6/1994 | Russek | |
| 5,319,698 A | 6/1994 | Glidewell et al. | |
| 5,321,963 A | 6/1994 | Goldman | |
| 5,327,478 A | 7/1994 | Lebowitz | |
| 5,333,173 A | 7/1994 | Seazholtz et al. | |
| 5,343,509 A | 8/1994 | Dounies | |
| 5,351,235 A | 9/1994 | Lahtinen | |
| 5,382,948 A | 1/1995 | Richmond | |
| 5,390,238 A | 2/1995 | Kirk et al. | |
| 5,398,277 A | 3/1995 | Martin, Jr. et al. | |
| 5,398,782 A | 3/1995 | Talbot et al. | |
| 5,400,246 A * | 3/1995 | Wilson et al. | 340/3.1 X |
| 5,402,466 A | 3/1995 | Delahanty | |
| 5,404,577 A * | 4/1995 | Zuckerman et al. | 455/66 |
| 5,410,292 A | 4/1995 | Le Van Suu | |
| 5,412,372 A | 5/1995 | Parkhurst et al. | |
| 5,416,695 A | 5/1995 | Stutman et al. | |
| 5,421,178 A | 6/1995 | Hamel et al. | |
| 5,432,841 A | 7/1995 | Rimer | |
| 5,440,301 A | 8/1995 | Evans | |
| 5,451,839 A | 9/1995 | Rappaport et al. | |
| 5,485,504 A | 1/1996 | Ohnsorge | |
| 5,486,812 A | 1/1996 | Todd | |
| 5,507,162 A | 4/1996 | Chhatwal | |
| 5,513,111 A | 4/1996 | Wortham | |
| 5,543,778 A | 8/1996 | Stouffer | |
| 5,552,641 A | 9/1996 | Fischer et al. | |
| 5,568,535 A | 10/1996 | Sheffer et al. | |
| 5,570,083 A | 10/1996 | Johnson | |
| 5,583,831 A | 12/1996 | Churchill et al. | |
| 5,587,701 A | 12/1996 | Hess | |
| 5,630,207 A | 5/1997 | Gitlin et al. | |
| 5,633,910 A | 5/1997 | Cohen | |
| 5,640,147 A | 6/1997 | Chek et al. | |
| 5,652,564 A | 7/1997 | Winbush | |
| 5,687,215 A | 11/1997 | Timm et al. | |
| 5,689,236 A | 11/1997 | Kister | |
| 5,698,095 A | 12/1997 | Kami | |
| 5,712,619 A | 1/1998 | Simkin | |
| 5,719,551 A | 2/1998 | Flick | |
| 5,736,932 A | 4/1998 | Bulfer et al. | |
| 5,739,748 A | 4/1998 | Flick | |
| 5,742,233 A | 4/1998 | Hoffman et al. | |
| 5,752,976 A | 5/1998 | Duffin et al. | |
| 5,754,111 A | 5/1998 | Garcia | |
| 5,777,551 A | 7/1998 | Hess | |
| 5,778,315 A | 7/1998 | Proietti | |
| 5,782,118 A | 7/1998 | Chamberlain et al. | |
| 5,784,685 A | 7/1998 | Stanford et al. | |
| 5,786,746 A | 7/1998 | Lombardo et al. | |
| 5,793,283 A | 8/1998 | Davis | |
| 5,812,536 A | 9/1998 | Manduely | |
| 5,815,417 A | 9/1998 | Orr et al. | |
| 5,821,854 A | 10/1998 | Dorinski et al. | |
| 5,825,283 A | 10/1998 | Camhi | |
| 5,845,203 A | 12/1998 | LaDue | |
| 5,850,180 A | 12/1998 | Hess | |
| 5,850,344 A | 12/1998 | Conkright | |
| 5,852,408 A | 12/1998 | Christiansen et al. | |
| H1782 H | 2/1999 | Wicks et al. | |
| 5,870,020 A | 2/1999 | Harrison, Jr. | |
| 5,873,043 A | 2/1999 | Comer | |
| 5,874,889 A | 2/1999 | Higdon et al. | |
| 5,892,442 A | 4/1999 | Ozery | |
| 5,894,591 A | 4/1999 | Tamayo | |
| 5,898,391 A | 4/1999 | Jefferies et al. | |
| 5,898,904 A | 4/1999 | Wang | |
| 5,902,234 A | 5/1999 | Webb | |
| 5,907,279 A | 5/1999 | Bruins et al. | |
| 5,917,405 A | 6/1999 | Joao | |
| 5,933,080 A | 8/1999 | Nojima | |
| 5,933,086 A | 8/1999 | Tischendorf et al. | |
| 5,936,544 A | 8/1999 | Gonzales et al. | |
| 5,940,007 A | 8/1999 | Brinkmeyer et al. | |
| 5,959,529 A | 9/1999 | Kail, IV | |
| 5,963,136 A | 10/1999 | O'Brien | |
| 5,969,595 A | 10/1999 | Schipper et al. | |
| 5,983,347 A | 11/1999 | Brinkmeyer et al. | |
| 6,014,626 A | 1/2000 | Cohen | |
| 6,023,223 A | 2/2000 | Baxter, Jr. | |
| 6,023,241 A | 2/2000 | Clapper | |
| 6,028,514 A | 2/2000 | Lemelson et al. | |
| 6,029,286 A | 2/2000 | Funk | |
| 6,035,021 A | 3/2000 | Katz | |
| 6,035,217 A | 3/2000 | Kravitz | |
| 6,038,896 A | 3/2000 | Chamberlain et al. | |
| 6,044,257 A | 3/2000 | Boling et al. | |
| 6,057,758 A | 5/2000 | Dempsey et al. | |
| 6,072,402 A | 6/2000 | Kniffin et al. | |
| 6,078,785 A | 6/2000 | Bush | |
| 6,084,510 A | 7/2000 | Lemelson et al. | |
| 6,087,952 A | 7/2000 | Prabhakaran | |
| 6,089,058 A | 7/2000 | Elpern et al. | |
| 6,118,866 A | 9/2000 | Shtivelman | |
| 6,147,622 A | 11/2000 | Fonea | |
| 6,150,942 A | 11/2000 | O'Brien | |
| 6,161,005 A | 12/2000 | Pinzon | |
| 6,168,563 B1 | 1/2001 | Brown | |
| 6,211,787 B1 | 4/2001 | Yoshiike et al. | |
| 6,234,343 B1 | 5/2001 | Papp | |
| 6,240,394 B1 | 5/2001 | Uecker et al. | |
| 6,243,010 B1 | 6/2001 | Addy et al. | |
| 6,288,641 B1 | 9/2001 | Casais | |
| 6,294,999 B1 | 9/2001 | Yarin et al. | |
| 6,295,346 B1 | 9/2001 | Markowitz et al. | |
| 6,305,377 B1 | 10/2001 | Portwood et al. | |
| 6,340,928 B1 | 1/2002 | McCurdy | |
| 6,346,889 B1 | 2/2002 | Moss | |
| 6,356,192 B1 * | 3/2002 | Menard et al. | 340/539.19 |
| 6,377,810 B1 | 4/2002 | Geiger et al. | |
| 6,388,559 B1 | 5/2002 | Cohen | |
| 6,388,612 B1 | 5/2002 | Neher | |
| 6,442,241 B1 | 8/2002 | Tsumpes | |
| 6,480,147 B2 | 11/2002 | Durst et al. | |
| 6,529,723 B1 | 3/2003 | Bentley | |
| 6,553,236 B1 | 4/2003 | Dunko et al. | |
| 6,563,910 B2 | 5/2003 | Menard et al. | |

| | | |
|---|---|---|
| 6,571,103 B1 | 5/2003 | Novakov |
| 6,591,094 B1 | 7/2003 | Bentley |
| 6,608,557 B1 | 8/2003 | Menard et al. |
| 6,615,414 B2 | 9/2003 | Miller et al. |
| 6,667,688 B1 | 12/2003 | Menard et al. |
| 6,668,284 B1 | 12/2003 | Parkhurst |
| 6,671,351 B2 | 12/2003 | Menard et al. |
| 6,687,517 B2 | 2/2004 | Kinnunen |
| 6,720,861 B1 | 4/2004 | Rodenbeck et al. |
| 6,728,341 B1 | 4/2004 | Puchek et al. |
| 6,759,956 B2 * | 7/2004 | Menard et al. ........ 340/539.19 |
| 2001/0011224 A1 | 8/2001 | Brown |
| 2001/0025208 A1 | 9/2001 | Bartur |
| 2001/0044731 A1 | 11/2001 | Coffman et al. |
| 2001/0056226 A1 | 12/2001 | Zodnik et al. |
| 2001/0056502 A1 | 12/2001 | Hollstrom et al. |
| 2002/0016722 A1 | 2/2002 | Kameda |
| 2002/0017996 A1 | 2/2002 | Niemiec |
| 2002/0080029 A1 | 6/2002 | Menard et al. |
| 2002/0098874 A1 | 7/2002 | Zirul et al. |
| 2002/0137460 A1 | 9/2002 | Sun et al. |
| 2002/0169539 A1 | 11/2002 | Menard et al. |
| 2002/0177428 A1 | 11/2002 | Menard et al. |
| 2002/0178385 A1 | 11/2002 | Dent et al. |
| 2002/0180582 A1 | 12/2002 | Nielsen |
| 2002/0183008 A1 | 12/2002 | Menard et al. |
| 2003/0013503 A1 | 1/2003 | Menard et al. |
| 2003/0016129 A1 | 1/2003 | Menard et al. |
| 2003/0091158 A1 | 5/2003 | Puchek et al. |
| 2003/0156028 A1 | 8/2003 | Menard et al. |
| 2003/0160681 A1 | 8/2003 | Menard et al. |
| 2003/0210140 A1 | 11/2003 | Menard et al. |
| 2004/0036573 A1 | 2/2004 | Fitzgibbon et al. |
| 2004/0066302 A1 | 4/2004 | Menard et al. |
| 2004/0100374 A1 | 5/2004 | Menard et al. |
| 2004/0218732 A1 | 11/2004 | Menard et al. |
| 2004/0247086 A1 | 12/2004 | Menard et al. |

OTHER PUBLICATIONS

"allNetDevices:—The Device–Centric Home in 2000: Close, But No Cigar", *allNetDevices*, http://www.devices.internet.com,(2000),3 pages.

"ARM7 Thumb Family", *Arm Powered*, Product Information,(Prior to May 26, 2000),4 pgs.

"ARM9 Thumb Family", *Arm Ltd.*, Product Information, (Prior to May 26, 2000),6 pgs.

"Automatic Crash Notification", *ComCare Alliance*, http://www.comcare.org/overview.htm,(2000),2 pages.

"Blue–Connect", *Acer NeWeb Corporation*, Product Brief, (prior to May 26, 2000),1 pg.

"Blue–Share", *Acer NeWeb Corporation*, Product Brief, (prior to May 26, 2000),1 pg.

"Bluetooth—Solutions for Personal Area Networking", *TDK Systems, Inc.*. Manufactures Brochure,(Prior to May 26, 2000),4 pgs.

"Bluetooth Development using SDL, MSC and TTCN", *Teleogic AB*, Product Information,(Prior to May 26, 2000), 13 pgs.

"Bluetooth Product Design—A Natural Progression of Our Existing Business", *RTX*, Manufactures Brochure,(Prior to May 26, 2000),4 pgs.

"Bluetooth White Paper", *AU–System AB*, (1999),Entire Pamphlet.

"Connect 24 Data Communications", *Connect 24*, http://www.connect24.com,(2001),1 page.

"CreataLink", *Motorola, Inc.*, (1999),2 pages.

"CreataLink 2XT", *Motorola Messaging Products*, www.mot.com/MIMS/MSPG/Products/OEM/calxt/,(Mar.1999),1 p.

"CreataLink 2XT", *Motorola*, http://www.motorola.com/MIMS/MSPG/Products/OEM/calxt/,(Mar.1999),1 page.

"Designing Solutions for the Internet Economy", *Intel Developer Forum Spring 2000*, Program Brochure, (Feb.15–17, 2000),2 pages.

"Digianswer Bluetooth—Development and Demonstration Tools", *DIGIANSWER A/S*, Product Sheet,(Prior to May 26, 2000),6 pgs.

"DIGIANSWER/Bluetooth Technology", *Digainswer (Irl)Ltd.*, Product Inforamtion.(Prior to May 26, 2000),6 pgs.

"Emergency 911 Cellular Phone and Cellular Phone Accessories", *AAA Communications*, http://web.idirect.com/aaa/, (2001),1–7 pages.

"Emergency Terms", *Glossary*, http://www.comcare.org/glossary.htm,(2000),3 pages.

"Empowering the mobile enterprise",*Puma Technology, Inc.*, Manufactures Brochure,(1996–1999),2 pages.

"Emulation System Speeds Development of CDMA Satcom Handsets", *Penton Publishing, inc.*, Product Inormation, (1997), 4 Pages.

"Enabling Innovation", *Arm Ltd.*, Product Brochure,(1999), 10 Pages.

"Freehand Remote Control Lock", *Remote Control Lock Instruction Manual*, KDL, Inc.,(1997),pp.1–15.

"Get a better vantage point and outmaneuver the competition", *Cadence Design Systems, Inc.*, Manufactures Brochure,(1999),6 pgs.

"Introduction to the HomeRF Technical Specification", *HomeRF,* (2000),pp. 1–17.

"IVT—Bluetooth Protocol Stack SDL/C Source Code", *Bluthtooth,* Product Brochure,(Prior to May 26, 2000),2 pgs.

"Lucent Technologies and Bluetooth", *Lucent Technologies, Inc.*, Manufactures Brochure,(Dec. 1999),2 pages.

"ObjectGEODE—The Most Advanced Integrated Enviornment for the Development of Distributed Real–time Systems", *VERILOG S.A.*, (1998),12.

"Office Action mailed by the US PTO on Aug. 15, 2000 for related matter U. S. Appl. No. 09/384,165", 29 Pages.

"Office Action mailed by the US PTO on Mar. 26, 2003 for related matter U. S. Appl. No. 09/956,474", 9 Pages.

"Office Action mailed by the US PTO on Oct. 3, 2003 for related matter U. S. Appl. No. 09/956,474", 5 Pages.

"ORA Electronics Introduces Rescue Mate, a Complete Cellular Telephone Safety Package", *Business Wire*, http://www.findarticles.com,(1998),2 pages.

"ORA Electronics Introduces Rescue MAte, a Complete Telephone Package", *Business Wire*, http://www.findarticles.com,(1998),2 pages.

"OSE—the new generation realtime operating system", *ENA OSE Systems*, Infomational Brochure,(1999),Entire booklet.

"PSAP updates and Third–Party Call Centers", *ComCARE Alliance*, http://www.comcare.org/psap/htm,(2000),2 pages.

"Samsung Electronics joins home radio frequency group in development of wireless network for the home", *Samsung Electronics*, http://www.samsung.com/news/samsung/1998/sea0305.htm,(1998),2 pgs.

"Socket's Bluetooth Cordless Communications Card FAQ", *Socket Communications, Inc.*, Informational Literature, (Dec. 1999),2 pages.

"Spontaneous Connections", *CommVerge*, (May 2000), 6 pages.

"Tachless Remote Engine Starters", *Almex*, http://www.almexltd.com/iei/mantis1200.htm,(2000),pp. 1–3.

"Technology Solutions for Bluetooth from Ericsson Microelectronics", *Erricson Components AB*, Manufactures Brochure,(Nov. 1999),2 pages.

"The Ericsson Bluetooth Development Kit—Faster Launching of Bluetooth Products", *Ericsson Mobile Communications, AB*, Manufactures Brochure,(1999),2 pgs.

"The Secret of Success!", *SIGnal Newsletter—The Official Newsletter of the Bluetooth Special Interest Group*, Issue No. 3,(Nov. 1999),8 pgs.

"UMTS W–DCMA Technology Development Using the Aptix System Explorer MP4 for Algorithm Verification", *Aptix Corporation*, Product Information,(1999),4 Pages.

"Unleash the World—Core technology for Bluetooth applications", *Ericsson Mobile Communications AB*, Manufactures Brochure,(1999),7 pgs.

"Will the push—not pull—of Internet information dramatically alter our Web Interaction", *SunWorld*, http://www.sunworld.com,(2000),6 pgs.

"Wireless Connections Made Easy", *Bluetooth*, Manufactures Brochure,(Prior to May 26, 2000),19 pgs.

"Your Vision—Our Solution", *RTX Telcom*, Manufactures Brochure,(prior to May 26, 2000),5 pgs.

Fitzgibbon, J. J., . "Method and Apparatus for Providing Access to a Dwelling Via a Remote Signal", Filed: Jan. 12, 2000, U.S. Appl. No. 60/175,749, 22 pgs.

Houston, Jerry , "Socket Teams with Cambridge Silicon Radio for Bluetooth Cordless Networking on Windows CE", *Socket Communications, Inc.*, Press Release,(1999),2 pages.

Menard, R. J., "Detection System Using Personal Communication Device with Response", U.S. Appl. No. 11/006,507, filed Dec. 7, 2004.

Menard, R. J., et al., "Interactive Motion Sensitive Sensor", U.S. Appl. No. 10/290,097, filed Nov. 7, 2002.

Menard, R. J., et al., "Long Range, Bidirectional, Wireless Personal Communication System", U.S. Appl. No. 09/277,805, filed Mar. 27, 1999.

Menard, R. J., et al., "Modular Communication System and Method", U.S. Appl. No. 09/579,913, filed May 26, 2002.

Nobel, Carmen, "Microsoft jumps on the Bluetooth bandwagon", *PC Week*, (Dec. 6, 1999),1 page.

Posti, J. , "Motorola Introduces CreataLink 2 XT ReFLEX Two–way Data Transceiver for Wireless Communications", *Motorola Press Release*, www.mot.com/MIMS/MSPG/Press/PR19990303_21575.html,(Mar. 1999),2 p.

"ARM7 Thumb Family", *Arm Powered*, Product Information, 4 Pages, (Prior to May 26, 200).

"ARM9 Thumb Family", *Arm Ltd.*, Product Information, 6 Pages, (Prior to May 26, 200).

"Blue–Connect", *Acer NeWeb Corporation*, Product Brief, 1 page, (Prior to May 26, 200).

"Blue–Share", *Acer NeWeb Corporation*, Product Brief, 1 page, (Prior to May 26, 200).

"Bluetooth—solutions for personal area networking", *TDK Systems, Inc.*, Manufactures Brochure, 4 pages, (Prior to May 26, 200).

"Bluetooth Development using SDL, MSC and TTCN", *Teleogic AB*, Product Information, , 13 Pages, (Prior to May 26, 200).

"Bluetooth Product Design—a natural progression of our existing buy", *RTX*, Manufactures Brochure, 4 pages, (Prior to May 26, 200).

"Bluetooth White Paper", *AU–System AB*, Entire Pamphlet, (1999).

"CreataLink", *Motorola, Inc.*, 2 pages, (1999).

"CreataLink 2XT", *Motorola Messaging Products*, www.mot.com/mims/mspg/Products/oem/calxt/, 1 pg., (Mar. 1999).

"Designing Solutions for the Internet Economy", *Intel Developer Forum Spring 2000*, Program Brochure, 2 pages, (Feb. 15–17, 2000).

"Digianswer Bluetooth—Development and Demonstration Tools", *DIGIANSWER A/S*, Product Sheet, 6 pages, (Prior to May 26, 200).

"DIGIANSWER/Bluetooth Technology", *Digianswer (Irl)Ltd.*, Product Information, 8 Pages, (Prior to May 26, 200).

"Empowering the mobile enterprise", *Puma Technology, Inc.*, Manufactures Brochure, 2 pages, (1996–1999).

"Emulation System Speeds Development of CDMA Satcom Handsets", *Penton Publishing, inc.*, Product Inormation, 4 Pages, (1997).

"Enabling Innovation", *Arm Ltd.*, Product Brochure, 10 Pages, (1999).

"Get a better vantage point and outmaneuver the competition", *Cadence Design Systems, Inc.*, Manufactures Brochure, 2 pages, (1999).

"IVT—Bluetooth Protocol Stack SDL/C Source Code", *Bluethtooth*, Product Brochure, 2 pages, (Prior to May 26, 200).

"Lucent Technologies and Bluetooth", *Lucent Technologies, Inc.*, Manufactures Brochure, 2 pages, (Dec. 1999).

"ObjectGEODE—The Most Advanced Integrated Environment for the Development of Distributed Real–time Systems", *VERILOG S.A.*, Entire Brochure, (1998).

"OSE—the new generation realtime operating system", *ENA OSE Systems*, Infomational Brochure, Entire booklet (1999).

"Socket's Bluetooth Cordless Communications Card FAQ", *Socket Communications, Inc.*, Informational Literature, 2 pages, (Dec. 1999).

"Spontaneous Connections", *CommVerge*, 6 pages, (May 2000).

"Technology Solutions for Bluetooth from Ericsson Microelectronics", *Ericsson Components AB*, Manufactures Brochure, 2 pages, (Nov. 1999).

"The Ericsson Bluetooth Development Kit—Faster Launching of Bluetooth Products", *Ericsson Mobile Communications, AB*, Manufactures Brochure, 2 pages, (1999).

"The Secret of Success!", *SIGnal Newsletter—The Official Newsletter of the Bluetooth Special Interest Group*, Issue No. 3, 8 Pages, (Nov. 1999).

"UMTS W–DCMA Technology Development Using the Aptix System Explorer MP4 for Algorithm Verification", *Aptix Corporation*, Product Information, 4 Pages, (1999).

"Unleash the World—Core technology for Bluetooth applications", *Ericsson Mobile Communications AB*, Manufactures Brochure, 8 pages, (1999).

"Wireless Connections Made Easy", *Bluetooth*, Manufactures Brochure, 19 Pages, (Prior to May 26, 200).

"Your Vision—Our Solution", *RTX Telcom*, Manufactures Brochure, 6 pages, (Prior to May 26, 200).

Houston, J., "Socket Teams with Cambridge Silicon Radio for Bluetooth Cordless Networking on Windows CE", *Socket Communications, Inc.,* Press Release, 2 pages, (1999).

Nobel, C., "Microsoft jumps on the Bluetooth bandwagon", *PC Week,* 1 page, (Dec. 6, 1999).

"CreataLink 2XT", *Motorola Messaging Products,* www.mot.com/MIMS/MSPG/Products/OEM/calxt/, 1 p., (Mar. 1999).

Posti, J., "Motorola Introduces CreataLink™ 2 XT ReFLEX™ Two–way Data Transceiver for Wireless Communications", *Motorola Press Release,* www.mot.com/MIMS/MSPG/Press/PR19990303_21575.html, 2 p., (Mar. 1999).

\* cited by examiner

COMMUNICATIONS

| NETWORK MODULE |
| --- |
| SHORT RANGE MODULE |

FIG. 3A

COMMUNICATIONS

| NETWORK MODULE |
| --- |

FIG. 3B

COMMUNICATIONS

| SHORT RANGE MODULE |
| --- |

FIG. 3C

| NUMBER OF BITS | OPTION COUNT | DESCRIPTION |
|---|---|---|
| 3 | 8 | DESTINATION CODE, FOR EXAMPLE A LIST OF OPTIONAL CENTRAL STATION AND USER DESTINATIONS IS STORED IN THE WIRELESS NETWORK. THE DESTINATION CODE TELLS THE NETWORK WHICH OPTIONAL DESTINATION SET (8 TOTAL LOOKUP SETS) TO USE FOR THIS MESSAGE. A SET MAY INCLUDE ONE OR MORE POTENTIAL DESTINATIONS. |
| 0-2 | 0-4 | BACKUP DESTINATION CODE: DESIGNATES A BACKUP DESTINATION OPTION IF THE MESSAGE IS UNDELIVERABLE TO THE PRIMARY DESTINATION. THE NETWORK STORES THE BACKUP DESTINATION. THIS INFORMATION COULD BE OPTIONALLY STORED IN THE NETWORK DESTINATION CODE LOOKUP SET DESCRIPTION. |
| 4 | 16 | TYPE OF MESSAGE CODE: THIS DESIGNATES THE TYPE, MEANING OR CONDITION OF THE MESSAGE BEING SENT. FOR EXAMPLE, FIRE, BURGLARY, MEDICAL WOULD ALL BE DESIGNATED ALARM TYPES OR CONDITIONS. THE NETWORK WOULD USE THE DESIGNATED LOOK UP TABLE FOR THE TRANSMITTER INVOLVED IN ORDER TO TRANSLATE THE MESSAGE (IF NECESSARY) BEFORE DELIVERY. OTHERWISE, THE MEANING CAN BE TRANSLATED UPON RECEIPT WITH A DESIGNATED LOOK UP TABLE THERE. |
| 2-4 | 4-16 | MODIFIER CODE: THIS DESIGNATES FURTHER INFORMATION ABOUT THE MESSAGE CODE. FOR EXAMPLE, STATUS INFORMATION, LOCATION (BY ZONE OF DETECTION OR AREA) INFORMATION OR OTHER INFORMATION. |

FIG. 9

BI-DIRECTIONAL WIRELESS DETECTION SYSTEM

RELATED APPLICATIONS

This application is a continuation of U.S. patent Ser. No. 09/956,474, filed Sep. 19, 2001, now U.S. Pat. No. 6,759,956, which is a continuation of U.S. patent application Ser. No. 09/384,165, filed on Aug. 27, 1999, now issued as U.S. Pat. No. 6,356,192, the specifications of which are incorporated herein by reference. This application also claims the benefit under 35 USC § 119(e) of U.S. Provisional Application No. 60/105,493, filed Oct. 23, 1998, and U.S. Provisional Application No. 60/135,862, filed May 25, 1999, the specifications of which are incorporated herein by reference.

FIELD OF THE INVENTION

The present invention relates generally to security, alarm or detection systems and wireless systems; and in particular to a bidirectional wireless detection system.

BACKGROUND

The provision of a security alarm detection system generally requires several components and a rather complex installation. Consequently, most detection systems require professional installation and setup.

Some of the current designs try to integrate many or all of the components and devices in a single enclosure or case. However, much of the complexity and cost remains since most of the devices and components are still in use.

Occasionally a detection system actuates automatic systems such as fire suppression or equipment shutdown, but in order for a detection system to be effective it usually must summon help. One approach for summoning help is to annunciate a local alarm that attracts attention. Another is to use a recorded message that is called to a list of phone numbers. Yet another is to use a professional central station monitoring service that receives data signals from the premise. As alarms, false alarms, and the indifference of neighbors increases, voluntary response to an alarm sound has virtually vanished. Hence local alarm annunciation is ineffective for garnering assistance. Indeed, the sound of an alarm has come to be perceived more as a nuisance and annoyance than a cause for attention. In a similar fashion, recorded messages are outlawed in a large number of 911 emergency dispatch centers and counting on reaching someone at home is not reliable. In addition, false alarms make recorded messages an irritation, especially since they are designed to repeat. So recorded messages are likewise considered ineffective. This leaves the use of a professional monitoring service which is inherently expensive and so many properties are left completely unprotected.

As a result, very low market penetration exists for reasons associated with current design. These include, but are not limited to, the requirement for professional design, the requirement for professional installation, and the requirement for professional monitoring. These three reasons make even so called "do-it-yourself" systems relatively poor sellers and even several major consumer electronic companies such as Magnavox, Zenith, Radio Shack and others have had little success or outright failure with an over the counter, table-top type product.

Furthermore, for correct installation of a standard security system to a telephone network, some tabletop models require a special phone jack (RJ-31X) installed at the correct location (before any premise equipment is connected to the line) to assure the availability of the phone line. This may require installation by a telephone company or other professional. In addition, services on the user's line can interfere with successful alarm transmission, with touch tone service, call waiting, and in the future, Digital Subscriber Line services will make the connection even more complex.

A related problem is found in the user's interface with the detection system. In a typical system, the user interacts with the detection system through a device generally known as a keypad. The current keypad designs do not allow the user to roam broadly and one long-range design—the telephone line connection—does not provide for messages to user that are initiated by the system, instead the user independently calls into the system to retrieve messages or interact with the system. Although some alarm systems in use today can initiate a page to a person's pager, this still does not allow the user to exercise command and control functions in return. There is no single device that allows long-range, bidirectional communication and control of an alarm system.

What is needed in the art is an improved detection system that is friendly to a mobile user, that is easy to install, that is truly portable, and that is inexpensive, without the high costs associated with professional design, expert installation, and monitoring services.

SUMMARY

One skilled in the art will readily recognize that the embodiments described solve all of these problems and many more not mentioned expressly herein.

In one embodiment, the detection system provides, among other things, a personal control panel and a portable detection unit which may be used independently or with a bidirectional communications network for short range and long range control panel and alarm monitoring and control functions. Several variations are provided including cellular, paging, satellite, narrowband PCS, narrowband trunked radio, and other communications systems with conventional and nonconventional protocols.

In one embodiment, the present detection system provides, among other things, the replacement of any or all of the user interface, transmission system, and control panel as listed above, through the use of a long-range, two-way, wireless communication device such as a two-way pager. Accordingly, a person who owns a two-way pager or related device, may, for a much lower cost than is customary, own a detection system by incorporating only an additional paging/detection device as described herein. This embodiment of the system has the advantages, including, but not limited to, simple installation, reliable and secure built-in signal transmission, long range wireless user interface and long range system status annunciation. Currently, many detection systems communicate with a central station that manages the response function. However, this embodiment of the present system offers yet another advantage by communicating direct to the system owner who may then select the desired response. In one embodiment, the direct communications are optional so that the owner may select the central station approach or the direct approach without the services of a central station. Thus, the present system provides, among other things, instant and affordable protection for a wide variety of applications such as construction sites, vehicles, motel rooms, apartments, and small residential and commercial properties.

Furthermore, in one embodiment, the system incorporates low power components to provide the additional advantage of being able to operate solely on battery power for extended periods of time and not just as an emergency/temporary backup.

Thus, the present system, in various embodiments, offers advantages over a standard detection system which include, but are not limited to: low cost; easy, instantaneous installation by an ordinary consumer; reliable communications without connection to or interruption of the site telephone lines; long range control by the user; long range communication of alarm conditions and other signals to a user; long range wireless communication to a central station included instead of as an option; no requirement for connecting to a central station with its attendant monthly costs, if the user desires to monitor their system themselves; and, no need for a permanent power supply. Thus, the system and its various embodiments offers a portable detection system that can provide protection for a variety of applications including, but not limited to, homes and businesses, and to applications without power or phone lines like vehicles and construction sites.

This summary is intended to provide a brief overview of some of the embodiments of the present system, and is not intended in an exclusive or exhaustive sense, and the scope of the invention is to be determined by the attached claims and their equivalents.

DESCRIPTION OF THE DRAWINGS

FIG. 3A is a block diagram of a communications module according to one embodiment of the present system.

FIG. 3B is a block diagram of a communications module according to one embodiment of the present system.

FIG. 3C is a block diagram of a communications module according to one embodiment of the present system.

FIG. 9 is a table depicting a sample message splitting or parsing strategy for parsing messages using the short message feature of ReFLEX™ (a Motorola Trademark) networks.

DETAILED SYSTEM DESCRIPTION

This detailed description provides a number of different embodiments of the present system. The embodiments provided herein are not intended in an exclusive or limited sense, and variations may exist in organization, dimension, hardware, software, mechanical design and configuration without departing from the claimed invention, the scope of which is provided by the attached claims and equivalents thereof.

The present system provides many benefits, including but not limited to, low cost, easy installation, limited power requirements and wireless operation and signal transmission. Many other benefits will be appreciated by those skilled in the art upon reading and understanding the present description.

U.S. Provisional Patent Application No. 60/098,392, filed Aug. 29, 1998; U.S. Provisional Patent Application No. 60/098,270 filed Aug. 28, 1998; U.S. Provisional Patent Application No. 60/105,493 filed Oct. 23, 1998; and U.S. Provisional Patent Application No. 60/135,862 filed May, 25, 1999, are all hereby incorporated by reference in their entirety.

Figure 1:
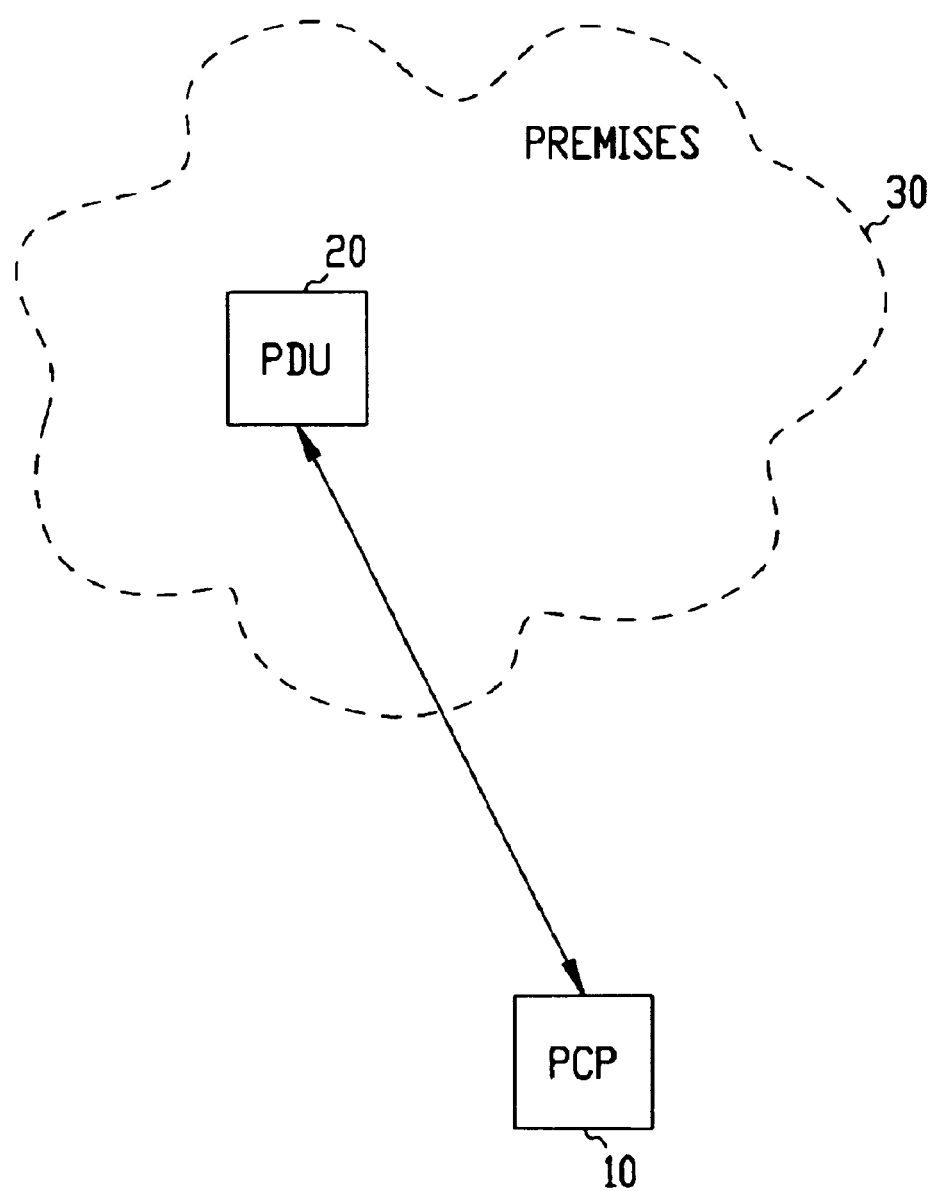
FIG. 1 is a diagram demonstrating operation of a personal control panel and portable detection unit according to one embodiment of the present system.

FIG. 1 shows one example of a premises 30, such as a house, garage, yard, warehouse, vehicle or any fixed, portable, or mobile location or structure intended for detection monitoring. A Portable Detection Unit 20 ("PDU 20") is located in or on the premises 30 for detection or monitoring of one or more events or conditions. Detection of events and status of the PDU 20 is communicated to Personal Control Panel 10 ("PCP 10"). PCP 10 is shown "off premises" but may be used "on premises" as well. The PCP 10 is useful for monitoring the condition of the PDU 20 and for reception of detected events. PCP 10 is also useful for, among other things, transmitting information to PDU 20 for the purposes of either arming the PDU 20, disarming PDU 20, and/or cancelling an alarm deemed false by the user of PCP 10. In one embodiment, PCP 10 and PDU 20 communicate using a short range communication device which is dedicated for such communications and which also may include a limited range, such as approximately that of the premises. Other short range embodiments are possible without departing from the present system. In one embodiment, PCP 10 and PDU 20 communicate using a combination of short range communications and long range communications, depending on the distance of PCP 10 from PDU 20. In yet another embodiment, PCP 10 and PDU 20 communicate using a long range communication system, even if the communications are conducted in proximity. Such a system incorporates an existing wireless communications network, such as a cellular network, satellite network, paging network, narrowband PCS, narrowband trunk radio, or other wireless communication network. Combinations of such networks and other embodiments may be substituted without departing from the present system.

Figure 2:
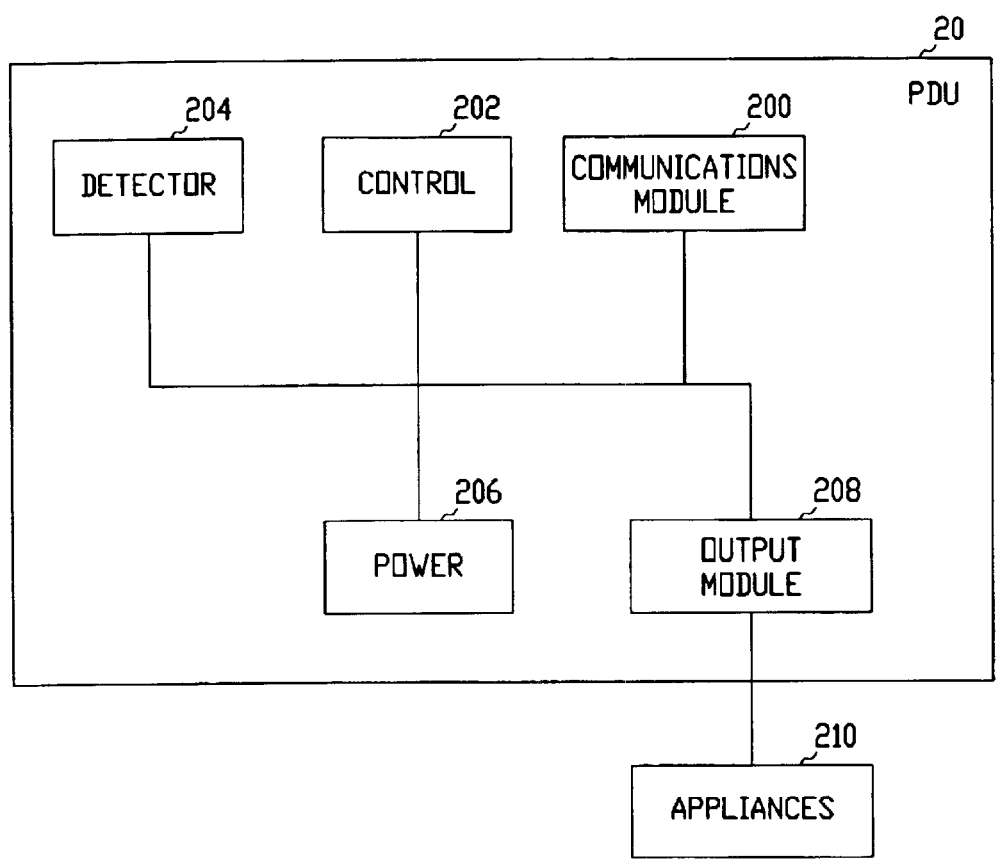
FIG. 2 is a block diagram of a portable detector unit according to one embodiment of the present system.

FIG. 2 shows one embodiment of a PDU 20 which includes a communications module 200, a control 202, one or more detectors 204, and power 206. In one embodiment PDU 20 is a self powered detector capable of communications with a PCP 10 in one embodiment, a wireless communications network (not shown in FIG. 2) in another embodiment, or both a PCP 10 and a wireless communications network in yet another embodiment. Other embodiments and combinations are possible without departing from the present system.

In the PDU 20 shown in FIG. 2, there is a detector 204 which detects events, including, but not limited to, motion detection, temperature detection, water detection, vibration detection, breakage detection, smoke detection, carbon monoxide detection, and proximity detection. Other detectors or combinations of detectors may be used without departing from the present system. In various embodiments, control 202 coordinates communications between the communications module 200 and the outside world (such as PCP 10 or a wireless communication network, for example). Control 202 may also process instructions received by communications module 200 regarding arming the PDU 20, disarming PDU 20, and cancellation of alarms, to name a few operations. With control 202, several operations may be performed using multiple detectors.

In one embodiment, the PDU 20 includes an output module 208 which provides control outputs to auxiliary devices and appliances 210. The outputs may be used to actuate an audible or visual annunciator in the premise such as an alarm. In other applications the outputs may be connected to appliances to provide actuation or control. The outputs may be signaled by changes in voltages, impedance, current, magnetic field, electromagnetic energy such as radio frequency signals, infrared signals or optical signals, and audible or other forms of mechanical energy. The outputs may be direct changes of state, analog, or digital in form. Several embodiments are possible, and the examples given herein are not intended in a limiting or restrictive sense. The output module may be activated and controlled by the PCP 10 or the control 202, or by the actuation of the detector 204 or a combination of these.

In one embodiment the PDU 20 is self powered. In one embodiment the PDU 20 is powered using an auxiliary power supply. In one embodiment the PDU 20 is charged using an auxiliary power supply.

FIG. 3A, FIG. 3B and FIG. 3C demonstrate a variety of short range and long range communications modules 200 in various embodiment examples. For instance, in FIG. 3A, the communication modules 200 includes a short range module, such as a bidirectional short range communication system with a network module. The network module may be used either for long range communications over a wireless communications network or for short range communications where the network is also used. Such a system may include programmable or automatically selecting electronics to decide whether to conduct communications between the PDU 20 and the outside world using the short range module or the network module. In one embodiment the system may employ different portions of the network to provide short range, intermediate range, or long range network connections, depending on the distance between the PDU and any receiving component of the system, such as PCP or central station. In one such embodiment, the network automatically adjusts for different required transmission distances.

In one embodiment, the network module is a cellular communications module. In one embodiment, the network module is a paging module, for example, a two-way paging module. In one embodiment the network module is a satellite module. In one embodiment the network module is a wideband or narrowband PCS module. In one embodiment the network module is a wideband or narrowband trunk radio module. Other modules are possible without departing from the present system. In one embodiment, the network module supports multiple network systems, such as a cellular module and a two-way paging module, for example. In such embodiments, the system may prefer one form of network communications over another and may switch depending on a variety of factors such as available service, signal strength, or types of communications being supported. For example, the cellular module may be used as a default and the paging module may take over once cellular service is either weak or otherwise unavailable. Other permutations are possible without departing from the present system.

FIG. 3B shows an embodiment including a network module. The variations in embodiments of network modules and uses of each described above apply here as well.

FIG. 3C shows an embodiment where a short range communications module is used for conducting communications between the PDU 20 and the outside world. Any conventional and nonconventional bidirectional short range communications may be employed for short range communications.

Figure 4:
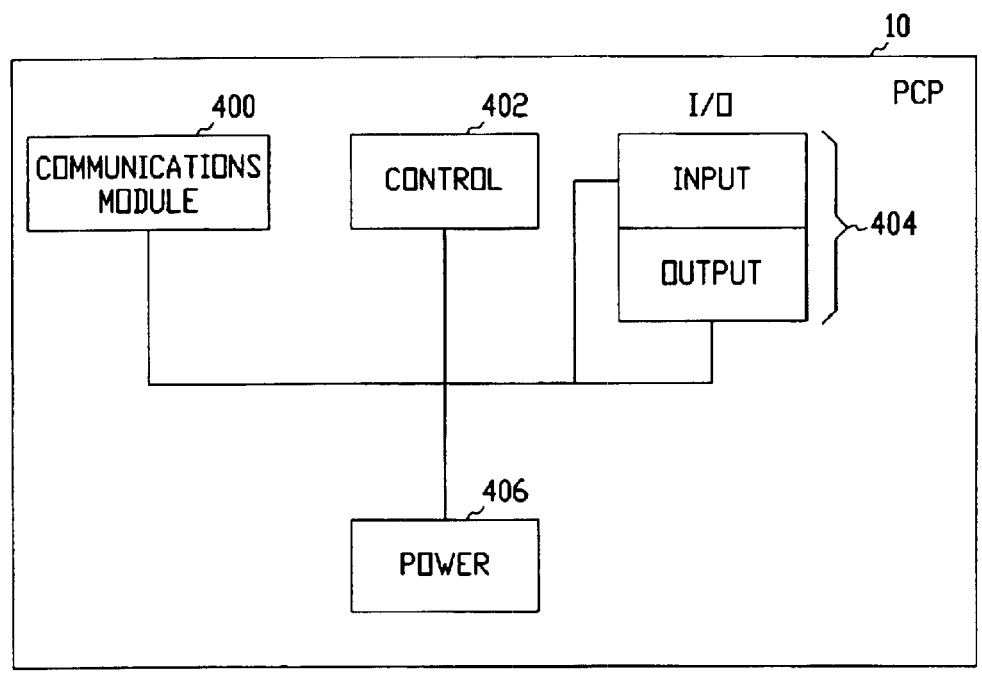
FIG. 4 is a block diagram of a personal control panel according to one embodiment of the present system.

FIG. 4 shows a block diagram of one embodiment of a PCP 10 having communications module 400, control 402, I/O 404 and power 406. In one embodiment, the PCP 10 has a counterpart communications module to PDU 20 so that the communications are possible using the same communication means. For example, if PDU 20 has a network module and a short range module, as shown in FIG. 3A, then PCP 10, in this embodiment, includes a network module and a short range module, capable of supporting bidirectional communications between PDU 20, PCP 10, and possibly a wireless communication network. In other embodiments, the PCP 10 need not have counterpart communications modules 400 to those in PDU 20.

Control 402 of PCP 10 is used to coordinate instructions entered on I/O 404 for transmission to the PDU 20 using communication module 400. In one embodiment I/O 404 is a keypad for entering instructions with a display for viewing status information. In one embodiment an audio indicator is used to signal a detected event. In one embodiment a visual indicator is used to signal a detected event. In one embodiment a vibration indicator is used to signal a detected event. In one embodiment separate indicators are provided for a plurality of detection functions.

In one embodiment, the power supply of PCP 406 is used to power the device. In one embodiment, the PCP 10 is powered using an auxiliary power supply. In one embodiment the PCP 10 is charged using an auxiliary power supply.

Figure 5:
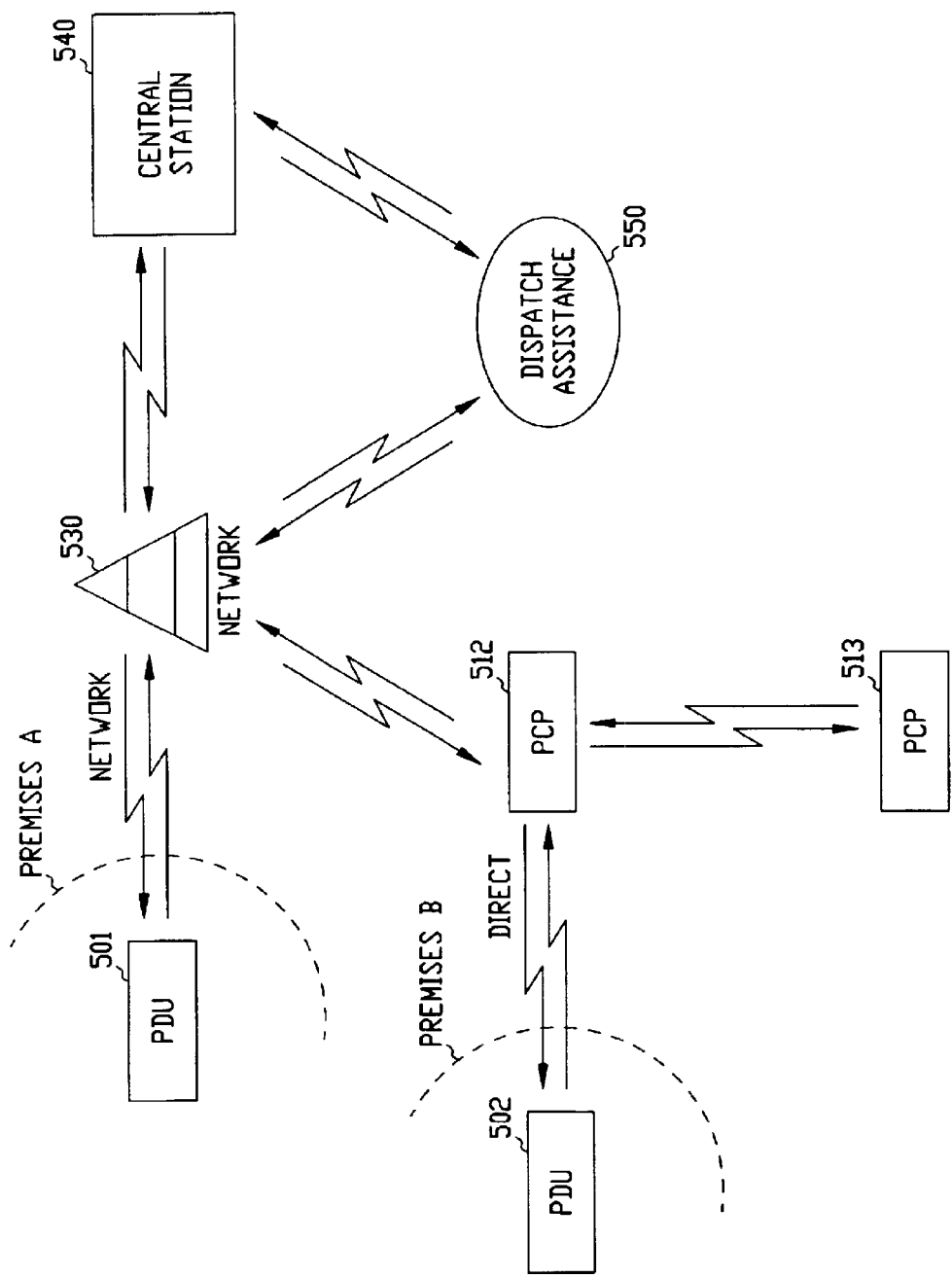
FIG. 5 is a diagram showing various communication modes of different components of one detection system according to one embodiment of the present system.

FIG. 5 is a diagram demonstrating different communication modes possible with the present system according to one embodiment. In this figure PDU 501 at premises A may communicate over a wireless communication network 530 to transceive signals relating to detected events with central station 540 or PCP 512. If PCP 512 is in range for short range communications, then PCP 512 may receive signals directly from a PDU, such as PDU 502 shown at premises B in FIG. 5.

PCP 512 may also communicate with other PDUs and with other PCPs, such as PCP 513. In FIG. 5 the communications between PCP 512 and PCP 513 are not shown over network 530, however, such communications are possible in various embodiments of the present system. In like manner, PDUs may communicate with multiple PCPs, not all possessing identical communication modules. Inter-protocol and inter-network communication may be managed separately, for example, both paging and cellular networks and modules communicate with each other through an IP-based protocol, such as over the Internet.

In one embodiment, PCP 513 is programmable to assume the identity of another PCP, such as PCP 512. When PCP 513 assumes the identity of PCP 512, it acts as if it were PCP 512 to the external world. One application where this is particularly useful is for when the native PCP becomes disabled or failed to operate. In this case, another PCP with the proper authorization and access code is used to perform any monitoring and/or control function. There are several methods of assuming identity: In one embodiment, PCP 512 and PCP 513 are part of a trusting domain of a network. In another embodiment, PCP 512 and PCP 513 are friends in the sense of object methodologies. In another embodiment, PCP 513 assumes the identity of PCP 512 by entering a certain security code, such as a password. In another embodiment, PCP 513 includes an alias of PCP 512, where aliases of PCP 512 have the same security clearance of access as PCP 512. In another embodiment, PCP 513 is an alias of PCP 512, where aliases of PCP 512 have a predetermined level of security clearance of access of PCP 512. These examples are no exclusive or exhaustive and other embodiments exist that do not depart from the present systems and methods.

In one embodiment wireless communication network 530 is a cellular telephone network. In another embodiment wireless communication network 530 is a two-way paging network. In one embodiment wireless communication network 530 is a satellite network. In one embodiment wireless communication network 530 is a wideband or narrowband PCS network. In one embodiment wireless communication network 530 is a wideband or narrowband trunk radio network. Other networks are possible without departing from the present system. In one embodiment, wireless communication network 530 supports multiple network systems, such as cellular mode and a two-way paging network, for example. In such embodiments, the system may prefer one form of network communications to another and may switch depending on a variety of factors such as available service, signal strength, or types of communications being supported. For example, the cellular network may be used as the primary network and the paging network may take over once cellular service is either weak or otherwise unavailable. In another embodiment the transmission may originate in one type of network such as a paging network and terminate in another type of network such as a cellular network. The symbol for wireless communication network 530 is not intended to be limited to literally a single communication tower and may include a plurality of such towers and associated wired telephone, ISDN, fiber optic, and other communications infrastructures in various combinations. Such systems may employ conventional or specialized protocols without departing from the present system. For example, MOTOROLA Corporation has introduced two way paging protocols such as ReFLEX 25 and ReFLEX 50. Other protocols and wireless communication networks may be employed without departing from the present system.

Security

In the situation where alarms are provided for detected events, the central station 540 may receive such alarms and process them for dispatch assistance 550 from emergency personnel. In one embodiment, false alarms are identified and cancelled prior to transmission to the central station by an operator of a PCP, such as PCP 512 or PCP 513. Systems for alarm cancellation and monitoring are provided in this disclosure and in the patent applications incorporated by reference herein.

In embodiments for security detection, the security industry has developed numerous types of detection devices for monitoring many types of conditions. These detection devices feature an output which changes state upon detection of the event being monitored by the device.

One embodiment of the present system uses the output of such detection devices and connects them as an input signal for a two-way, long-range, wireless communicator such as one employing narrowband PCS (two-way paging), cell phone type transmitter, PCS, cellemetry, or other similar device. The detection devices include, but are not limited to, motion detectors, door switches, water sensors, smoke detectors, temperature sensors, or a loop(s) of detection devices to detect a condition or occurrence and provide an output. The outputs may be signaled by changes in voltages, impedance, current, magnetic field, electromagnetic energy such as radio frequency signals, infrared signals or optical signals, and audible or other forms of mechanical energy. The outputs may be direct changes of state, analog, or digital in form. Several embodiments are possible, and the examples given herein are not intended in a limiting or restrictive sense.

The present system, in several embodiments, provides the signals from the detection devices to the two-way, long-range, wireless communicator instead of connecting them to a security alarm control system.

In one embodiment, the detection system incorporates on-site, a long-range two-way wireless communication devices which are compatible for communications with a two-way wireless communication device that is carried by the system user. The system user then utilizes their communication device to control and receive messages from the detection system. In one embodiment, the on-site communication device may trigger local annunciators like horns or flashing lights or actuate other equipment such as heating lights or mechanical equipment.

Figure 6:
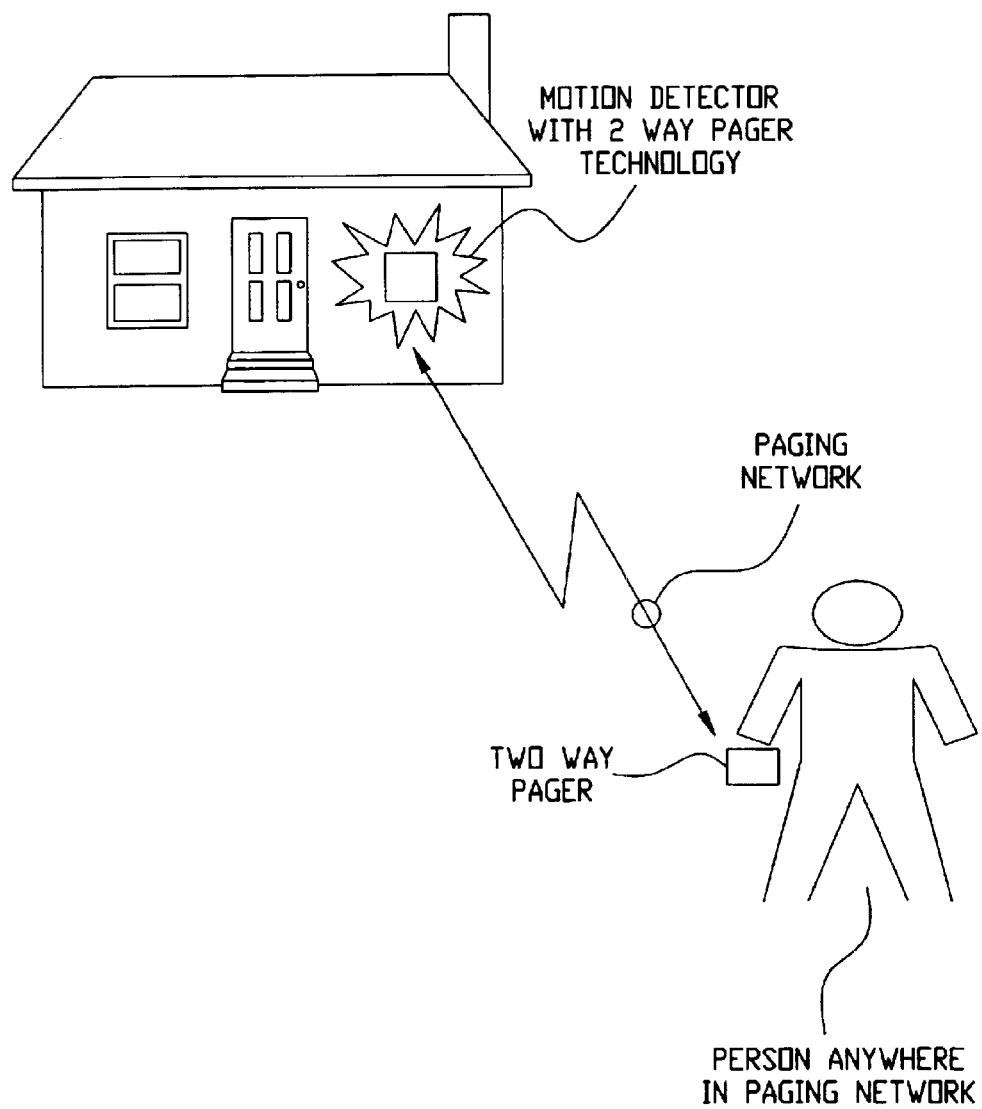
FIG. 6 is a diagram showing a user controlling their detection system from a distance, according to one embodiment of the present system.

FIG. 6. shows one embodiment of the present design in a detection system wherein a motion detector located in a home is connected to a two-way communications device, such as one employing two-way paging communication capabilities. The motion detector provides a signal to the two-way pager when detecting motion. The two-way pager transmits a signal over the paging network to the owner anywhere in the paging network. In one embodiment, if the person carries a two-way pager, then the person may elect to perform a function in response to the detected event, for example to disarm the detector by providing the proper command to the motion detector over the two-way paging network. Other embodiments are possible without departing from the present system and a number of functions may be supported by various embodiments of the present detection system.

Figure 7:
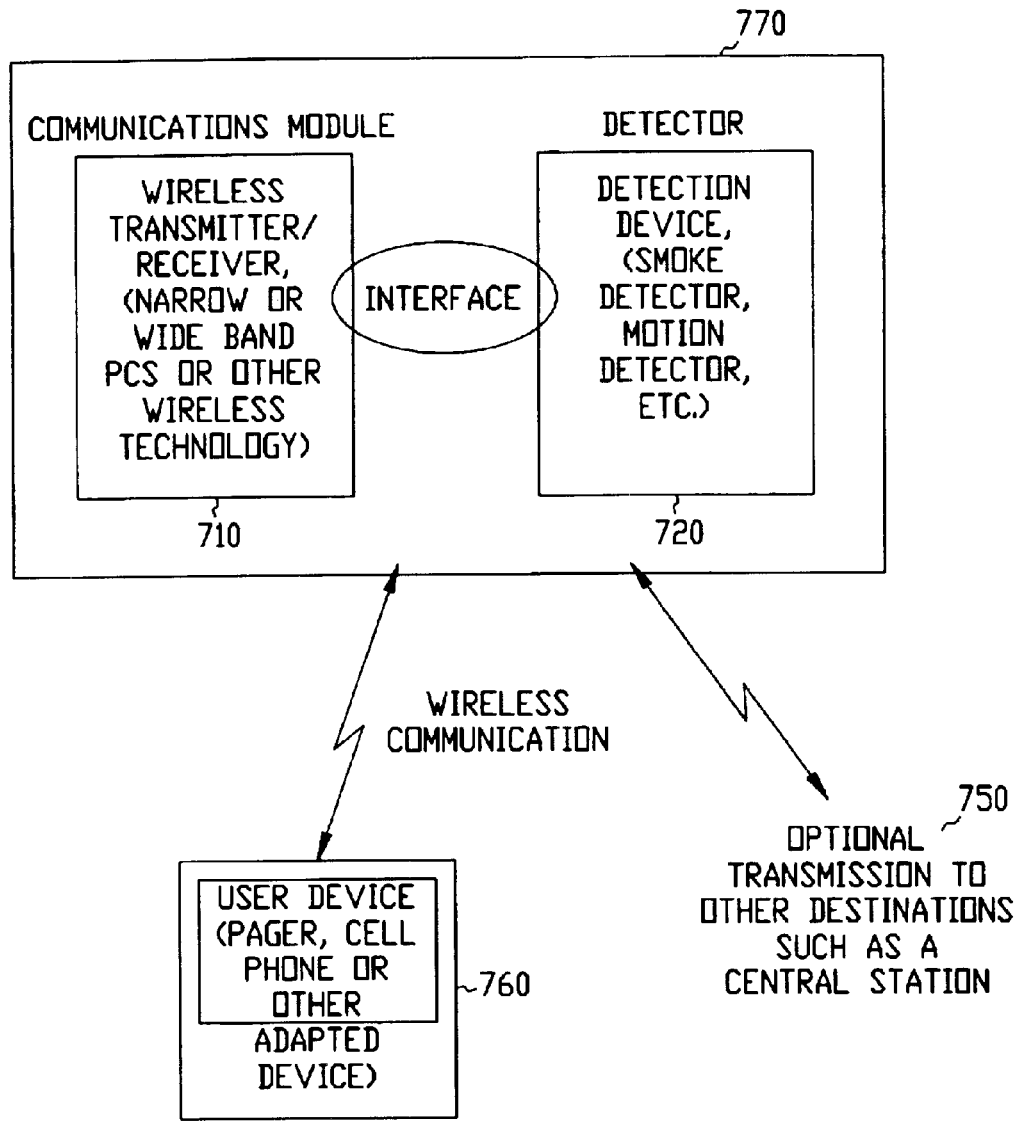
FIG. 7 is a block diagram showing the components of a basic security system, according to one embodiment of the present system.

FIG. 7 shows a block diagram of a detection system according to one embodiment of the present system. The block diagram shows the relationship between the communication module 710 and the detector 720 in PDU 770. The two way pager 760 may serve as the PCP in this system. It can be used to monitor alarms, disarm the system and to cancel false alarms, among other things. The system provides for optional transmission to other destinations 750, which may be accomplished over a wireless bidirectional communication network, among other things.

Wireless Network

The wireless network employed may be any consumer or proprietary network designed to serve users in range of the detection system, including, but not limited to, a cellular network such as analog or digital cellular systems employing such protocols and designs as PCS, CDMA, TDMA; a paging network such as those employing FLEX™ or POCSAG™; other data networks such as RAMNET™ or Ardis™; proprietary special design networks such as Alarmnet™ or Procom™; or proprietary wireless networks.

In one embodiment the detection system incorporates ReFLEX™ (a Motorola™ trademark) 25 or 50 narrow band PCS products and services (types of wireless technologies used for 2-way pagers). The advantage to this type of technology is that it requires low power consumption for devices, has inexpensive devices, and provides flexible 2-way communication.

PDU Communications Module

In one embodiment, a pager-like device, such as a device employing pager or other 2-way long range wireless communication capabilities, is connected to one or more detection devices. The interface between these devices is designed to function with standard manufactured detection devices using for example, but not limited to, small control relays or voltage triggers, or a standard communication protocol like RS-232, or built as a single integrated circuit with a detection device and thus requiring no external interface. The relay/voltage trigger embodiment provides a design that can be easily adapted to a wide array of existing detection devices or a circuit loop of devices. The integrated circuit embodiment provides a low net cost if the device is produced in large quantities.

In one embodiment the 2-way pager device located at the protected location is a CreataLink™ as manufactured by Motorola company. These are a series of intelligence enhanced 2-way narrowband PCS modems operating with ReFLEX 25 or ReFLEX 50 protocols. These products are being constantly upgraded and currently being manufactured as CreataLink2; soon to be manufactured as CreataLink2XLT. The CreataLink device is incorporated with other sensors and control circuitry as needed to provide one version of a PDU. The CreataLink devices may be modified and adapted for use with detectors and other bidirectional wireless network communication modules, as provided in herein.

PCP

In one embodiment, the users are in two-way communication with their detection system via a wireless means in order to provide the highest assurance of contact wherever the user may be. This allows the user to be informed of detected events and to control the detection system from in, nearby, or distant from the location of the premises.

The PCP may be of several different designs. For example, in one embodiment it may be a standard pager or other one-way wireless device. This would function satisfactorily for a user needing only annunciation of a detected condition and requiring no interactive capability with the detecting portion of the system.

In another embodiment, the PCP may be a "response messaging" capable two way pager. This is service where a two way pager receives a message and optional multiple-choice responses. The user can select the appropriate responses. Such a design may be adapted to provide basic control options related to the detection system and any central station monitoring.

In another embodiment, the PCP may be a programmable two-way paging device such as the Motorola PageWriter™ 2000. This is a class of device that acts as both a two-way pager and a handheld computer also known as a PDA (Personal Digital Assistant).

In another embodiment, the PCP may be a cellular telephone. The PCP and the protected location device may communicate of compatible design may communicate with each other through the use of touch tones, digital information, voice messaging, or cellemetry technologies. The cell phone may be analog or digital in any of the various technologies employed by the cell phone industry such as PCS, or CDMA, or TDMA, or others. The cell phone may have programmable capability such as is found in a Nokia™ 9000 series of devices.

In embodiments where the user employs standard or adapted paging or cell phones as their PCP, security passwords are entered by using numeric or other keys on a phone. In the embodiment of a pager, a distinct order of pressing certain keys could provide the equivalent of a security code. For example, 3 short and 1 long on a certain key; or once on key 'a', once on key 'b', and once more on key 'a'.

In another embodiment, the PCP is a handheld computer. Many PDAs offer programmable capability and connectivity to various types of long-range wireless networks. Another example of this type of device is the Palmpilot™ or Palm series of devices manufactured by 3-COM™. In these embodiments where a programmable PCP is used such as a PalmPilot, PageWriter or programmable cell phone, the programmable nature of the devices facilitates the implementation of industry-standard designs and would allow for the development of a program written for the devices.

In another embodiment, a special manufactured device may be manufactured to serve the needs of the system user.

Network Modifications For a PCP With Both Long-Range Wireless Capability and Adapted Short-Range Wireless Capability In one embodiment the PCP employs an adaptation of the long-range capability of such devices to create a short-range wireless communication without full network intervention. Because much of the communication between the PCP and the PDU is in relatively close proximity, the wireless devices and/or the network may be adapted to communicate more directly instead of through the entire network. More direct communication speeds up the connection and reduces the burden of traffic in the network.

Such an implementation would have applications beyond the use as described for the detection system herein. It may be used for connecting between nearby users of pagers at the mall, parents to children in the neighborhood and between workers in a workplace.

In one embodiment narrowband PCS is used in two-way paging networks. For example using ReFLEX 25 or 50 protocols or similar services, nearby pager devices may communicate more directly between devices, rather than having to pass a message through the entire network. There are several alternative embodiments of this as detailed below.

In one embodiment, paging devices are modified to communicate directly with each other. Since ReFLEX protocols normally use different frequencies for transmission and reception to and from the network, the devices may not be used without some modification. For example, the transmission on frequency "a" by one paging device would not be received by another paging device expecting to receive on frequency "b". Therefore, in one embodiment the transmitting paging device may change its frequency before sending direct to another device. This is accomplished automatically or as a manual switch, either in software or otherwise.

In another embodiment, the transmission is routed to the first tower or just into the local network. Most paging carriers use satellites for transmission to and from localized areas. In this embodiment, traffic may avoid the satellite portion of the route and save traffic burden there.

In any of the previous embodiments of this section, the network is able to supervise traffic for billing and other purposes. In addition, in these embodiments, messages may be tagged as "direct connect" for routing purposes. See the information on messaging described herein.

In another embodiment, a separate short range wireless system is incorporated into a unified device employing both a short range wireless system and a long range wireless system. In this embodiment, a key fob type of device such as though currently used for unlocking automobiles and disarming detection systems is combined with a long range wireless device such as those described herein. This embodiment affords the advantage of a no-service-fee wireless connection for nearby use and a service-fee wireless network for long-range use.

PCP with Other Manufactured Systems

The various PCP design embodiments described herein may benefit the system described herein and also many other security, alarm, detection and control systems manufactured presently and in the past, rather than the PDU described herein. For example, in an embodiment using a two-way paging network, a Motorola PageWriter™ 2000 with an alarm program, may function as the user interface, while a CreataLink™ 2XT may provide the connection to the security, alarm, detection or control system as manufactured currently. In one embodiment, the CreataLink™ may be connected directly to a manufacturer's system's control panel using the I/O signals, the RS232 or TTL serial interface, or it may be connected using these ports through a separate interface board.

For example, in the security alarm industry, some alarm panels support control functions with simple I/O signals, some support RS232 or other serial interfaces, and many have a proprietary serial connection available for remote keypad control. In another embodiment with a custom interface board or with adapted programming in the alarm panel a device such as the CreataLink™ is connected to the alarm control panel. These teachings are applicable to all of the major security industry manufacturers of alarm control equipment, such as Ademco™, ITI™, DSC™, Napco™, Radionics™, DMP™, and many others.

Because of the tremendous variability of manufactured security, alarm, detection and control systems, and the range of PCPs, as described herein, available to control these systems, the details of each and every specific design would be virtually endless. Hence, the embodiments provided herein are not intended in an exclusive or limited sense, and variations may exist in organization, dimension, hardware, software, mechanical design and configuration without departing from the claimed invention, the scope of which is provided by the attached claims and equivalents thereof.

Position Transmitted with Detected Condition

The design of the detection and control system with its low power requirements and bidirectional wireless communication capabilities makes it suited to mobile applications as well as the fixed applications previously discussed. However, the response required for a mobile application often requires knowledge of where the premises have moved. For example, in protecting vehicles such as automobiles, trucks, and boats, the protected item may have moved.

In one embodiment of the detection system, a GPS receiver is incorporated and the system transmits GPS coordinates along with the detection signals. In another embodiment of the detection system, other types of coordinates are transmitted such as with LORAN.

In one embodiment the user device may incorporate mapping capabilities for locating the mobile unit. In one embodiment the mapping capabilities may be resident in the user device or in another embodiment the maps may be downloaded from a central storage facility. In another embodiment a directional message could be displayed showing which direction and/or distance the detection signal emanated from. Such a coordinate may be updated from time to time.

Security Detection System Features

In one embodiment, the software in the PDU, the PCP, and the network is adapted to deliver the standard features of a typical detection, alarm, security, or detection system. These features are currently common to most manufacturers today, including ITI, Ademco, Napco, and others. Examples of these features include but are not limited to:

system on/off (home-away-off, arm-disarm),
delay zones,
bypass/force arm,
restore,
opening and closing by user,
prevention of multiple alarm transmissions in a specified period,
user control of system related functions, Thus, such embodiments provide features standard to a security alarm system without requiring a separate control panel to provide them. In addition, some of the embodiments provide enhancements to the standard features. One reason for the improvements is that a system user can provide interactive management functions of their system from the PCP regardless of where they are located. No longer do they need to be at the protected location. Some of the functions are discussed below, however, others exist and the following is not intended to be a limiting of exhaustive discussion of functions.

Zone Bypass. This feature allows a user to turn off the transmission of signals for a particular detector or group of detectors. This is done for the following common reasons:

1. When the user is on site and wants to retain some protection, for example intrusion detection, but wants to turn off some interior motion detectors.
2. When the person is prone to accidentally trigger a detector. For example, as listed in item 1, perhaps there is an interior motion detector downstairs, but they sleep upstairs; they would prefer to have the motion detector on while sleeping, but often forget and trip the detector when they come down in the morning.
3. When a person is first learning to use their system, sometimes the entire system is bypassed so emergency agencies are not dispatched.
4. When a zone seems to be prone to false-alarms and the source of the signals is not determined or repaired. The zone may send a real or a false alarm.

One problem with zone bypass is that it is an all-or-nothing design. The zone(s) or detector(s) is either transmitting signals or not. In one embodiment of the present system, a new type of condition, which we herein label "zone confirmation" is supported by the system. Conditions 2, 3, 4 above would be better served in many cases if the user was notified of an detected event and may then optionally "confirm" the condition before it was transmitted to the central station. This confirmation may be required, or it may have a built in delay period where an opportunity to cancel would be given before the alarm was transmitted. The user's confirmation or lack thereof may be transmitted to the central station and add valuable information to the response effort.

Arm/Disarm Confirmation. When a user armed or disarmed their system (turned their system on or off), confirmation of the on or off is sent back to the PCP that they are carrying and doing the activation from. This is currently not possible even with the short-range wireless devices used in the industry currently.

Delay Zones. Delay zones are built into detection control panels to provide time for a user to enter their code into a keypad or other device and then enter or exit the premise before the protection is activated. Because upon entry, this delay is activated, there is a desire to make the delay short. Otherwise an intruder might have time to tamper with or destroy the system before it transmits a signal.

However, delay zones may be built into the PCP instead. This would allow a user to optionally cancel or confirm an event condition before the network transmitted it forward to a central station or other site. As a result, the system would be effectively instantaneous, that is—continuously armed without delay zones, allowing an intruder no delay time to defeat a system, but allowing a user an opportunity to disarm the system.

Alarm Verification/Cancellation. Due to the large number of false alarms associated with security systems, it is ordinary for central monitoring centers to verify alarms with users before dispatching agencies. Since this detection system uses a method whereby the user can be in contact with the central monitoring station anywhere they are located, the verification could occur via the user's interface. Hence, an embodiment of the present system may incorporate special alarm verification/cancellation technology as described in U.S. Provisional Application No. 60/098,270, filed Aug. 28, 1998 and U.S. Patent Application Ser. No. 09/219,737, filed Dec. 22, 1998, both of which are hereby incorporated by reference in their entirety.

Other embodiments are possible and the examples provided herein are intended to be demonstrative and not exclusive or exhaustive of the present invention, which is determined by the scope of the appended claims and the full range of equivalents to which they are entitled.

System Messaging

Capcodes

In one embodiment using NPCS (Narrowband PCS) as the wireless transmission method, pager capcodes are used for addressing. Capcodes are the addresses used to identify individual addresses and there is a unique capcode for each pager or common pager address. In common addressing—pagers can hold more than one capcode for broadcast messaging—a common capcode identifies a group of users. For example, capcode 978654903 may uniquely indicate Joe Smith's pager while another capcode may also reside on Joe Smith's pager for broadcast receipt of the news or weather which is received simultaneously by multiple users with the same broadcast capcode. Therefore, capcodes are used to identify an individual user or group of users and likewise identify the detection system that is associated with the users.

Rapid Data Transmission

It is important that the data is received rapidly both to enhance protection and to help to provide rapid verification in order to cancel alarms. The transmission of data in this embodiment is done in a rapid burst method. The reason for this is as follows: As available in NPCS transmissions, for example with FLEX 25 and 50—two of the protocols currently available for NPCS services—there is a short message availability (11 bit) that allows for very rapid transmission. In cellular there is a technology called Cellemetry or Microburst that accomplishes a similar function. This short and rapid messaging is a feature of many large scale wireless networks. The short message is typically available to be sent immediately and rapidly and often at a lower cost. For example, in FLEX 25, longer messages require time to set up transmission frames. By using a short burst transmission, as much as 20 seconds or more may be saved in the transmission time requirement. This delay is of serious consequence because in the security industry, life and property may be in peril. In addition, delays make it difficult to coordinate the rapidly proceeding dispatch between the central station and the users. However, the short message has constraints of its own: it is a short message. Therefore, the message must be encoded. A solution for encoding in FLEX related services is presented later.

Hence, in one embodiment a short predetermined digitally encoded message is transmitted from the detection system to the PCP carried by remote users and/or to the central station.

Figure 8:
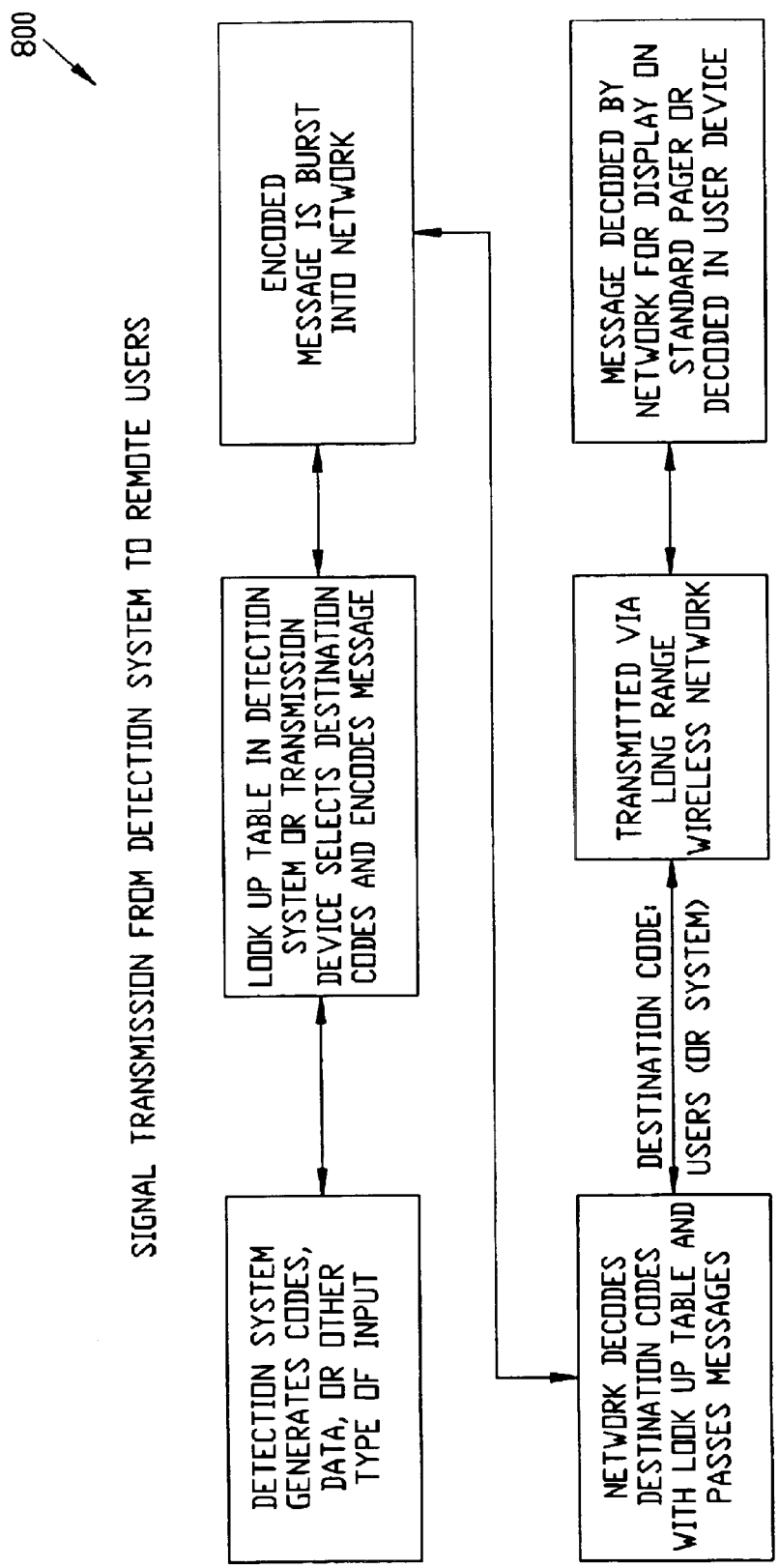
FIG. 8 is a flow chart showing the passing and processing of messages from the detection system to remote users.

At the central station a look up table is employed to decode the message. In a similar fashion, a look up table may be employed by the PCP to decode the message. FIG. 8 shows one such example of a look up table.

Message Decoding in the Network

Usually transmission networks are designed to simply receive a message and transport it to a destination. The network doesn't "read" the message or "act" on it except to read an address and send it to the destination. However, as networks become imbued with enhanced computing capability, they can read more of the message and process messaging far beyond mere transport.

Therefore, as an alternative embodiment, the look up table may reside in the network and the message may be decoded by the network before it is delivered to any destination. This is a good way for delivering a message to the PCPs unable to decode messages such as limited capability pagers or cell phones. The encoded burst message would then be decoded in the network and a user would be delivered an English or other language message according to the interpretation or look up table.

The effect is that an encoded burst message that looks like "00101000111" may be decoded in the network and read out "Burglary Area 4" on a pager. The same numeric message may be decoded after receipt in a more sophisticated user device or after receipt at the central station.

Alternative Message Paths

One embodiment of this design uses a single two way wireless device carried by the users instead of one device to receive the message and another to transmit the verification information to the central station. This saves cost and simplifies design. However, two separate devices may be used.

In other embodiments, the notification of the remote users may be accomplished simultaneously with the central station or instantly relayed by the central station or any other relay point.

Again, in one embodiment, the transmission of data may be done in a rapid burst method. In this process, a short predetermined digitally encoded message is transmitted to the central station from the user device.

Alternatively, longer messages can be employed, but they may take longer to be received.

In the event that NPCS is the selected wireless transmission method, a standard two way pager using response paging is used as the response device carried by the user to communication/control with the detection system and to the central station.

In this design option a response message can either be presaved on the two way pager or can be transmitted to the pager. Since time is important, a presaved response message is the best solution since it does not require any additional transmission time.

Other custom designed devices and devices using other wireless technologies can also be used to accomplish the same effect.

Encoding

Encoding is a straightforward process. The following encoding example is offered for the use of NPCS FLEX 25 two way pager wireless services.

In FLEX 25 an 11 bit message (an 11 bit message is eleven zeros or ones) is available for a burst transmission. This message is then split or parsed into registry sections for the purpose of sending a message. The table (FIG. 9) describes sample registers and their potential purpose.

As a result a message like "001/0111/0101" (slashes indicate breaks in the register of the look up table and are not transmitted) can be interpreted to mean: send a message to Joe Smith's pager capcode 957843756 reading "Fire area 5" and send a message "001/0111/0101" to Central Station A and send "001/0111/0101" Central Station B if Central Station A is not receiving.

The above register size, order, and meaning can be changed to meet the needs of individual network designs. However, the purpose and use remains unchanged. Similar encoding registers can be used in any wireless transmission short bursting format.

Conclusion

Other embodiments are possible and the examples provided herein are intended to be demonstrative and not exclusive or exhaustive of the present invention, which is determined by the scope of the appended claims and the full range of equivalents to which they are entitled.

We claim:

1. A system comprising:
a first portable detection unit including:
at least one detector to detect at least one event;
a detection controller coupled to the at least one detector; and
a detection bi-directional communications module coupled to the detection controller;
a first personal control panel including:
an input/output device;
a panel controller coupled to the input/output device; and
a panel bi-directional communications module coupled to the panel controller; and
a long-range, bi-directional, wireless network communicating between the detection bi-directional communications module and the panel bi-directional communications module.

2. The system of claim 1, wherein the detection bi-directional communications module includes a bi-directional short range communications module.

3. The system of claim 1, wherein the panel bi-directional communications module includes a bi-directional short range communications module.

4. The system of claim 1, wherein the detection bi-directional communications module includes a network module.

5. The system of claim 1, wherein the panel bi-directional communications module includes a network module.

6. The system of claim 1, wherein the first portable detection unit further comprises an output module controllable by at least the first portable detection unit.

7. The system of claim 1, wherein the first portable detection unit further comprises an output module controllable by at least the first personal control panel.

8. The system of claim 1, wherein the first portable detection unit further comprises an output module controllable by at least the first portable detection unit and the first personal control panel.

9. The system of claim 1, further comprising a second portable detection unit able to be located in a geographic location diverse from the first portable detection unit, wherein the first personal control panel is programmable to control one or more of the first portable detection unit and the second portable detection unit.

10. The system of claim 9, further comprising a second personal control panel that is capable of assuming an identity of the first personal control panel to gain a predetermined level of access to one or more of the first portable detection unit and the second portable detection unit.

11. The system of claim 1 wherein the input/output device is a keypad.

12. The system of claim 1 wherein the first personal control panel is a two-way pager.

13. The system of claim 12 wherein the detection bi-directional communications module and the panel bi-directional communications module communicate via Narrowband PCS (NPCS) protocol.

14. The system of claim 1 wherein the first personal control panel is a cellular telephone.

15. The system of claim 1 wherein the first personal control panel includes a handheld computer.

16. The system of claim 15 wherein the handheld computer is a Personal Digital Assistant (PDA).

17. The system of claim 1 wherein the first personal control panel is adapted to arm the at least one detector.

18. The system of claim 1 wherein the first personal control panel is adapted to disarm the at least one detector.

19. The system of claim 1 wherein the first portable detection unit is coupled to an appliance.

20. The system of claim 19 wherein the first personal control panel is adapted to control the appliance.

21. The system of claim 1 wherein the at least one detector includes a motion detector.

22. The system of claim 1 wherein the at least one detector includes a door switch.

23. The system of claim 1 wherein the at least one detector includes a water sensor.

24. The system of claim 1 wherein the at least one detector includes a smoke detector.

25. The system of claim 1 wherein the at least one detector includes a temperature sensor.

26. The system of claim 1 wherein the at least one detector includes a vibration detector.

27. The system of claim 1 wherein the at least one detector includes a breakage detector.

28. The system of claim 1 wherein the at least one detector includes a carbon monoxide detector.

29. The system of claim 1 wherein the at least one detector includes a proximity detector.

30. The system of claim 1, wherein the first portable detection unit further comprises an output module controllable by the first portable detection unit and by the first control panel.

31. The system of claim 30, wherein the first personal control panel comprises a cellular telephone.

32. The system of claim 31, further comprising a second personal control panel that is capable of assuming an identity of the first personal control panel to gain a level of access of the first portable detection unit.

33. The system of claim 32, wherein the second personal control panel comprises a cellular telephone.

34. The system of claim 1, wherein the detection bi-directional communications module includes a bi-directional short range communications module and the panel bi-directional communications module includes a bi-directional short range communications module.

35. The system of claim 34, wherein the detection bi-directional communications module includes a network module.

36. The system of claim 34, wherein the panel bi-directional communications module includes a network module.

* * * * *

UNITED STATES PATENT AND TRADEMARK OFFICE
CERTIFICATE OF CORRECTION

PATENT NO. : 6,960,998 B2  
DATED : November 1, 2005  
INVENTOR(S) : Raymond J. Menard and Curtis E. Quady It is certified that error appears in the above-identified patent and that said Letters Patent is hereby corrected as shown below:

Title page,
Item [56], References Cited, OTHER PUBLICATIONS,
"21st Century Emergency Safety Communication Policy" reference, delete
"21c199.htm" and insert -- 21ct99.htm --; and
"AlarmNet-M Mobitex System" reference, delete "1," and insert -- 1. --.

Signed and Sealed this

Twenty-eighth Day of March, 2006

JON W. DUDAS
*Director of the United States Patent and Trademark Office*